United States Patent
Koike et al.

(10) Patent No.: US 8,617,804 B2
(45) Date of Patent: Dec. 31, 2013

(54) METHOD OF DETECTING LEUKEMIC CELL

(75) Inventors: Takao Koike, Sapporo (JP); Mitsufumi Nishio, Sapporo (JP); Hiroshi Nishihara, Sapporo (JP)

(73) Assignee: National University Corporation Hokkaido University, Sapporo-shi (JP)

( * ) Notice: Subject to any disclaimer, the term of this patent is extended or adjusted under 35 U.S.C. 154(b) by 509 days.

(21) Appl. No.: 12/735,274

(22) PCT Filed: Dec. 24, 2008

(86) PCT No.: PCT/JP2008/073393
§ 371 (c)(1),
(2), (4) Date: Oct. 1, 2010

(87) PCT Pub. No.: WO2009/084525
PCT Pub. Date: Jul. 9, 2009

(65) Prior Publication Data
US 2011/0014636 A1    Jan. 20, 2011

(30) Foreign Application Priority Data
Dec. 28, 2007  (JP) .................... 2007-339228

(51) Int. Cl.
C12Q 1/00   (2006.01)
C12Q 1/68   (2006.01)
G01N 33/53  (2006.01)
G01N 33/574 (2006.01)

(52) U.S. Cl.
USPC .............. 435/4; 435/6.1; 435/6.14; 435/7.2; 435/7.23

(58) Field of Classification Search
None
See application file for complete search history.

(56) References Cited

PUBLICATIONS

Nishihara et al. (Blood Jun. 28, 2002 100: 3968-3974).*
Nishio et al. (Blood Nov. 16, 2008 112(11): 525).*
Harlow and Lane (Antibodies, a Laboratory Manual, Cold Spring Harbor Laboratory Press, 1988, p. 141-142).*
Answers (http://www.answers.com/topic/do-all-animals-have-blood, Jun. 5, 2013).*
Koki Kumano, "Study on expression of DOCK180 in human CD34 positive cells", Hokkaido Journal of Medical Science, Jan. 1, 2008, pp. 41-46, vol. 83, No. 1, Hokkaido University.
Koki Kumano et al., "DOCK180 expression in hematopoietic cells and association with . . . ", 70th General Meeting of the Japanese Society of Hematology, Sep. 30, 2008, p. 516.
Michiyuki Matsuda, "Study on molecular mechanism of carcinogenesis. . . ", Project Study Report on New 10 Year Strategy to Overcome Cancer, Mar. 31, 1997, pp. 59-66.
Michiyuki Matsuda, "Carcinogenesis mechanism by Crk cancer gene", Research Reports of Uehara Memorial Foundation, Nov. 20, 1999, pp. 181-182, vol. 13.
Mitsufumi Nishio et al., "Stem cell factor prevents Fas-mediated apoptosis . . . ", Experimental Hematology, 2001, pp. 19-29, vol. 29, Elsevier Science Inc.
Kazushi Inoue et al., "WT1 as a new prognostic factor and new markeer for . . . ", Blood, Nov. 1, 1994, pp. 3071-3078, vol. 84, No. 9, American Society of Hematology.

* cited by examiner

*Primary Examiner* — Peter J Reddig
(74) *Attorney, Agent, or Firm* — Hogan Lovells US LLP (57) ABSTRACT

[Problems] To provide a marker which is useful in diagnosing leukemia and a method of using the same.
[Means for Solving Problems] A method of detecting a leukemia cell which comprises detecting a CD34-positive cell being negative in DOCK180 expression from a blood specimen. According to this method, a DOCK180 expression pattern specific to a tumor cell in leukemia, in particular, acute leukemia is confirmed so that information which is useful in diagnosing leukemia and monitoring and determining the severity and degree of recovery of the same by a doctor can be obtained by a convenient procedure using blood specimens and thus provided.

10 Claims, 5 Drawing Sheets

|  | Type of disease | Onset / Recurrent | DOCK180 |
|---|---|---|---|
| 1 | ALL | Onset | 141 |
| 2 | ALL | Onset | 5 |
| 3 | ALL | Onset | 0 |
| 4 | ALL | Recurrent | 0 |
| 5 | ALL | Recurrent | 1 |
| 6 | ALL | Recurrent | 27 |
| 7 | ALL | Recurrent | 0 |
| 8 | AML | Onset | 751 |
| 9 | AML | Onset | 176 |
| 10 | AML | Onset | 1488 |
| 11 | AML | Onset | 30 |
| 12 | AML | Onset | 7 |
| 13 | AML | Onset | 0 |
| 14 | AML | Onset | 7 |
| 15 | AML | Onset | 3 |
| 16 | AML | Onset | 2 |
| 17 | AML | Onset | 68 |
| 18 | AML | Onset | 2 |
| 19 | AML | Onset | 1 |
| 20 | AML | Onset | 7 |
| 21 | AML | Onset | 273 |
| 22 | AML | Recurrent | 4346 |
| 23 | AML | Recurrent | 147 |
| 24 | CML. acute blastic crisis | Recurrent | 40 |
| 25 | CML. acute blastic crisis | Recurrent | 1740 |

METHOD OF DETECTING LEUKEMIC CELL

TECHNICAL FIELD

The present invention relates to a method of detecting leukemia, specifically acute leukemia, and a kit used in detecting leukemia.

BACKGROUND ART

Leukemia is a disease which belongs to hematologic malignancy, in which tumorigenic hemopoietic cells proliferate unlimitedly and appear in the blood. The disease called leukemia is mostly caused by tumorigenic leukoblasts, as well as by tumorigenic erythron and thrombocytic cells. In leukemia, there is a case that blood cells stop differentiation at a certain stage of differentiation or maturation, and undifferentiated blast cells in an upstream thereof proliferate to form tumor, while there is another case that blood cells retain an ability of differentiation or maturation despite deviation of biological regulatory ability and sign of autonomous growth. The former case corresponds to acute leukemia and the latter case to chronic leukemia or myelodysplastic syndromes (MDS). Though causes and pathogenic mechanisms are mostly unknown, it is vital to detect and treat leukemia at an early stage.

Leukemia is diagnosed e.g. by morphological observation of a blood cell, chromosomal test, or surface antigen analysis of a blood cell using flow cytometry. Meanwhile, concerning leukemia having chromosomal aberration or genetic aberration, PCR using disease-specific primer or RT-PCR is performed. It is also reported that the findings of quantitative RT-PCR of Wilms tumor gene 1 (WT-1) reflect the amount of tumor cells in leukemia (Non-Patent Document 1).

As stated above, leukemia treatment essentially requires early identification/detection, specifically that of leukemia or leukemia cells. Accordingly, this medical treatment heavily involves information of residual tumor cells (minimal residual disease (MRD)), found in e.g. the blood, particularly a bone marrow fluid, and its volume to judge therapeutic effects and determine required treatment policies.

Nevertheless, since morphological observation of a blood cell can confirm the existence of a tumor cell when its volume comes to a considerable amount, it is not appropriate for early detection of leukemia or detection of residual tumor cells. Surface antigen analysis of a blood cell using flow cytometry is expected to be effective in e.g. early detection of a tumor cell due to its favorable detection sensitivity and so on. Also, this analysis technique needs selecting a combination of cell surface antigens which are specific to a tumor cell and found on the surface thereof to be diagnosed. According to a quantitative RT-PCR of Wilms tumor gene 1 (WT-1), some cases demonstrated no expression level of the gene.

From the above observations, a method of examining leukemia in an easy and correct manner, particularly a method of examining leukemia having quantitativeness and less false positive, which is common to many kinds of leukemia, is constantly desired to be established.

Non-Patent Document 1
K. Inoue et al., Blood, 84 (9) 3071-3079 (1994)

DISCLOSURE OF THE INVENTION

Problem to be Solved by the Invention

The present invention provides a method of detecting leukemia or a leukemia cell in an easy and correct manner having quantitativeness and less false positive, using a selectable marker in leukemia, specifically in acute leukemia.

Means for Solving the Problem

The inventors found that concerning leukemia associated with a tumorigenic CD34-positive cell, DOCK180 expression which is observed in a normal CD34-positive cell declines or disappears and completed the following invention based on the related findings.

(1) A method of detecting a leukemia cell, comprising a step of detecting a CD34-positive cell whose expression of DOCK180 is negative in a blood specimen.
(2) The method of detecting a leukemia cell according to item (1), wherein a CD34-positive cell whose expression of DOCK180 is negative is detected according to an immunological detection method using an anti-CD34 antibody and an anti-DOCK180 antibody.
(3) The method of detecting a leukemia cell according to item (1) or (2), wherein a leukemia cell is an acute leukemia cell.
(4) The method of detecting a leukemia cell according to item (3), wherein an acute leukemia cell is an acute lymphocytic leukemia cell.
(5) A kit for detecting a leukemia cell, comprising an anti-DOCK180 antibody.
(6) The kit for detecting a leukemia cell according to (5), furthermore comprising an anti-CD34 antibody.
(7) A method of examining the degree of progression or regression of leukemia, comprising steps of detecting a CD34-positive cell whose expression of DOCK180 is negative in a blood specimen and measuring the proportion of said CD34-positive cells whose expression of DOCK180 is negative to CD34-positive cells whose expression of DOCK180 is normal.
(8) The method of examining the degree of progression or regression of leukemia according to (7), wherein CD34-positive cells whose expression of DOCK180 is normal and CD34-positive cells whose expression of DOCK180 is negative are detected according to an immunological detection method using an anti-CD34 antibody and an anti-DOCK180 antibody.
(9) The method of examining the degree of progression or regression of leukemia according to item (7) or (8), wherein leukemia is acute leukemia.
(10) The method of examining the degree of progression or regression of leukemia according to item (9), wherein acute leukemia is acute lymphocytic leukemia.
(11) A kit for examining the degree of progression or recovery of leukemia, comprising an anti-DOCK180 antibody.
(12) The kit for examining the degree of progression or recovery of leukemia according to item (11), furthermore comprising an anti-CD34 antibody.
(13) A method of detecting leukemia, furthermore comprising a step of measuring an expression level of DOCK180 in a CD34-positive cell in a blood specimen.
(14) The method of detecting leukemia according to item (13), wherein an expression level of DOCK180 in a CD34-positive cell in a blood specimen is measured, using an expression level of DOCK180 in a CD34-positive cell in a healthy blood specimen as an index value.
(15) The method of detecting leukemia according to item (13) or (14), wherein leukemia is acute leukemia.
(16) The method of detecting leukemia according to item (15), wherein acute leukemia is acute lymphocytic leukemia.
(17) A kit for detecting leukemia, comprising a nucleic acid that hybridizes with DNA encoding an anti-DOCK180 antibody or DOCK180.

(18) The kit for detecting leukemia according to item (17), furthermore comprising an anti-CD34 antibody.
(19) A method of examining the degree of progression or regression of leukemia, comprising a step of measuring an expression level of DOCK180 in a CD34-positive cell in a blood specimen.
(20) The method of examining the degree of progression or regression of leukemia according to item (19), wherein an expression level of DOCK180 in a CD34-positive cell in a blood specimen is measured, using an expression level of DOCK180 in a CD34-positive cell in a healthy blood specimen as an index value.
(21) The method of examining the degree of progression or regression of leukemia according to item (19) or (20), wherein leukemia is acute leukemia.
(22) The method of examining the degree of progression or regression of leukemia according to item (21), wherein acute leukemia is acute lymphocytic leukemia.

Advantageous Effect of the Invention

The present invention can provide information useful for diagnosis of leukemia, for consultation and diagnosis of the severity and degree of recovery of leukemia by a doctor, which can be obtained from blood specimens according to a convenient procedure, through confirmation of a DOCK180 expression pattern specific to a tumor cell in leukemia, particularly in acute leukemia.

BEST MODE FOR CARRYING OUT THE INVENTION

The present invention relates to a method of using the expression of a DOCK180 protein or a gene encoding the same as a marker for diagnosing leukemia, by defining a step of confirming, detecting and quantifying the expression of DOCK180 in a CD34-positive cell in a blood specimen as a key factor. As such, one embodiment of this invention is a method of detecting a leukemia cell, comprising a step of detecting a CD34-positive cell whose expression of DOCK180 is negative in a blood specimen. As stated above, in many tumorigenic CD34-positive cells, DOCK180 expression declines or disappears compared to that in a normal CD34-positive cell. This means that a CD34-positive cell whose expression of DOCK180 is negative can be determined as a tumorigenic cell. Thus, the result that such a tumorigenic CD34-positive cell was detected in a blood specimen, particularly in a bone marrow specimen according to the method of this invention provides information useful in judging whether the specimen is affected by leukemia or not.

Another embodiment of this invention is a method of examining the degree of progression or regression of leukemia, comprising steps of detecting a CD34-positive cell whose expression of DOCK180 is negative in a blood specimen, particularly in a bone marrow specimen and measuring the proportion of said CD34-positive cells whose expression of DOCK180 is negative to CD34-positive cells whose expression of DOCK180 is normal. For example, the results concerning the proportion of CD34 cells whose expression of DOCK180 is negative to the total number of CD34-positive cells contained per unit area of a blood specimen, particularly of a bone marrow specimen represent the degree of progression or regression of leukemia in the specimen, and serve as useful and objective information for a doctor to examine the severity and degree of recovery of leukemia in a patient.

Also, the present invention provides a method of detecting leukemia, comprising a step of measuring an expression level of DOCK180 in a CD34-positive cell in a blood specimen, particularly in a bone marrow specimen. This method is to measure e.g., an expression level of DOCK180 per unit volume of the entire CD34-positive cell, instead of detecting a CD34-positive cell whose expression of DOCK180 is negative in a blood specimen, particularly in a bone marrow specimen is negative. In particular, decline or subsequent increase in the measured level using an expression level of DOCK180 in a CD34-positive cell in a healthy specimen as an index value means that the examined specimen contains CD34-positive cells whose expression of DOCK180 is negative, or cells whose expression of DOCK180 is normal. Thus, such results can give a doctor information useful in judging whether a patient is affected by leukemia or not, or whether a patient is in remission or not. In other words, the degree of progression or regression of leukemia can be examined by measuring an expression level of DOCK180 in a CD34-positive cell quantitatively. The test results can be fully useful and objective information so that a doctor adequately diagnoses the severity and degree of recovery of leukemia of a patient.

"Blood specimen" in this invention is a broad term covering bone marrow fluid, peripheral blood collected from a vein, or blood-cell fraction specimen containing CD34-positive cells by centrifugal separation thereof and by a known chemical treatment for preparing a blood-cell fraction in accordance with a method described in Nishio et al. (Blood, 2005, Vol. 106, pp. 1012 to 1020). An embodiment of a blood specimen in this invention is preferably a bone marrow fluid, particularly a blood-cell fraction specimen fractionated from a bone marrow fluid.

A CD34-positive cell is, by definition, a hemopoietic progenitor cell having highly-expressed glycoprotein CD34 on the surface of a cell. The CD34-positive cell is contained in the blood, particularly in such as umbilical cord blood and bone marrow fluid, and can be detected and separated therefrom in accordance with a method described in Nishio et al. (Exp. Hematology, 2001, Vol. 29, pp. 19 to 29). Also, the CD34-positive cell can be separated using a separator from blood, etc., such as ISOLEX™ 300i (TAKARA BIO INC).

A DOCK180 in this invention is a type of protein for controlling the proliferation of higher eukaryotic animal cells that bind to a Crk protein which is protooncogene expression product. The DOCK180 is also known as a guaninenucleotide exchange factor (GEF) that activates low-molecular weight G protein called Rac. With a DNA encoding DOCK180 being already cloned, its base sequence and DOCK180 amino acid sequence are determined (see e.g. Patent Document 1: Japanese Unexamined Patent Application Publication No. 08-196277).

Since the binding of Crk protein and DOCK180 activates cell proliferation ability as conventionally shown, DOCK180 protein has received much attention as a diagnostic index of cancer cell expressing Crk protein and as a target for missile therapy, etc. by each anticancer agent. The inventors found that leukemia cells, particularly many tumorigenic CD34-positive cells are tumor cells whose expression of DOCK180 is negative, which was previously reported in a different manner.

"DOCK180 expression is negative in a CD34 cell" in this invention means that DOCK180 expression declines or disappears, more specifically that DOCK180 protein or mRNA encoding DOCK180 cannot be confirmed in a CD34-positive cell using ordinary methods for confirming gene or protein expression such as immunological detection method or genetic engineering techniques such as hybridization or PCR, even with a normal sensitivity. It also means that with a standard value of an expression level of DOCK180 in a normal CD34-positive cell, the expression level of DOCK180 protein or mRNA encoding DOCK180 is 50% or less, preferably 30% or less, more preferably 10% or less, much more preferably 5% or less. Also, "normal CD34-positive cell" and "DOCK180 expression is normal in a CD34 cell" in this invention mean a non-leukemia affected, i.e. non-tumorigenic CD34 cell, and a condition that DOCK180 expression is positive or an expression level thereof in said CD34-positive cell.

A term defined as DOCK180 in this invention denotes a protein comprising an amino acid sequence specifically described in said Patent Document 1, and a polymorphism-form DOCK180 as well when DOCK180 whose amino acid sequence is partially substituted by "single nucleotide polymorphism" exists.

Leukemia or leukemia cell in this invention means acute leukemia (both myeloid and lymphocytic), chronic leukemia (both chronic myeloid leukemia (CML) and chronic lymphocytic leukemia (CLL)), erythroleukemia, or leukemia such as thrombocythemia and its tumor cell, myelodysplastic syndromes (MDS) and its cell, particularly acute myeloid leukemia (AML), acute lymphocytic leukemia (ALL) and tumorigenic leukocyte.

Means of detecting DOCK180 expression or measuring its expression level in this invention is not particularly limited as long as it can exactly detect mRNA encoding DOCK180 protein and/or DOCK180 in a CD34-positive cell or measure its amount, but preferably an immunological detection means for DOCK180 protein, or a genetic engineering detection means for mRNA encoding DOCK180.

A method of detecting a DOCK180 protein using immunological detection means or a method of measuring its expression level is preferably used with an anti-DOCK180 protein antibody, particularly in combination with an anti-DOCK180 protein antibody and an anti-CD34 protein antibody. As such an antibody, all biomolecules can be used as long as they are understood by those skilled in the art as "antibody" such as polyclonal antibody, monoclonal antibody and Fab fragment, preferably monoclonal antibody in particular.

A monoclonal antibody can be produced using various monoclonal antibody production techniques known to those skilled in the art. As a common technique, a recombinant DOCK180 protein and a recombinant CD34 protein is produced according to genetic engineering technique known to those skilled in the art using sequence information described in said Patent Document 1. From an antibody-producing cell obtained according to an ordinary method of inoculating an animal therewith as an antigen and a myeloma cell, hybridoma is prepared to produce a monoclonal antibody. In addition, a polypeptide composed of partial sequence of an amino acid sequence of a DOCK180 protein and that of a CD34 protein may be used as an antigen. Existing commercially available anti-DOCK180 protein antibody and anti-CD34 protein antibody may also be used.

An antibody used in this invention using an immunological detection means is preferably labeled with a labeled substance. The labeled substance may be a substance which produces a detectable signal alone, or by reaction with other substances, e.g., enzymes such as horseradish peroxidase, alkaline phosphatase, β-D-galactosidase, glucose oxidase, glucose-6-phosphate dehydrogenase, alcohol dehydrogenase, malate dehydrogenase, penicillinase, catalase, apoglucose oxidase, urease, luciferase or acetylcholine esterase, fluorescent substances such as fluorescein isothiocyanate, phycobiliprotein, rare-earth metal chelate, dansyl chloride or tetramethylrhodamine isothiocyanate, radioisotopes such as $^{125}$I, $^{14}$C and $^{3}$H, chemical substances such as biotin, avidin or digoxigenin, or chemically luminescent materials. A method of labeling an anti-DOCK180 antibody with one or more of these labeled substances may be a known method according to a type of labeled substance to be selected.

This invention can employ the above antibody (incl. labeled ones) as an immobilized antibody which is immobilized on an insoluble carrier. Commonly used insoluble carriers include plates such as microplate in particular, test tube, tube, beads, bowl, filter, membrane, or cellulosic carrier, agarose carrier, polyacrylamide-based carrier, dextran-based carrier, polystyrene-based carrier, polyvinyl alcohol carrier, polyamino acid carrier, or insoluble carriers used in affinity chromatography such as porous silica-based carrier. A method of immobilizing an antibody on any one of these insoluble carriers may be a method conventionally established by each insoluble carrier.

A method of detecting DOCK180 protein or measuring an expression level thereof using an immunological detection means includes enzyme immunoassay method, radioimmunoassay method, flow cytometry analysis or western blott method. A principle, detailed test conditions and operational procedures thereof and a method of detecting an antigen-antibody complex are widely known to those skilled in the art, other than changes in a used antibody according to DOCK180 protein to be detected. In this invention, each of the above methods can be employed based on such conditions and procedures.

In this invention, immunoassay using an anti-CD34 antibody and an anti-DOCK180 antibody, particularly immunoassay using flow cytometry based on the two antibodies is preferable. Using flow cytometry, a CD34-positive cell whose expression of DOCK180 is negative and a CD34-positive cell whose expression of DOCK180 is normal are correctly distinguished and readily separated from each other. Also, a method in this invention or part thereof can be automated or semiautomated. The flow cytometry method is specifically described e.g. in Yamashita (Flow cytometory, Meneki-Kenkyuho (Immunization Research Method) Hand book, 1996, 2nd edition, pp. 247-262, Chugai-Igakusha), all of whose descriptions are included in this application.

A method of detecting DOCK180 expression or measuring an expression level thereof using genetic engineering detection means may be a method of detecting or quantifying mRNA encoding DOCK180 expressed in a blood specimen, and Southern hybridization, PCR techniques such as RT-PCR, real-time PCR and quantitative PCR can be used. A preferable method is PCR, and a particularly preferable method is quantitative is PCR by RT-PCR.

As a common technique, total RNAs extracted from a blood specimen according to a known method or mRNAs selected from all RNAs are subjected to PCR, for example to RT-PCR, using a polynucleotide corresponding to a base sequence encoding DOCK180 as an amplifying primer to amplify cDNA encoding DOCK180, and confirmation of an obtained amplification product and quantification of its volume are performed. The above PCR technique, including the design of a base sequence for amplifying a primer, based on a base sequence described in said Patent Document 1, is widely known to those skilled in the art. Accordingly, this invention can employ such a well-known method. As a technique for detecting or quantifying gene expression by PCR method, a number of PCR methods having various technological approaches have been reported in many researches, which may be employed in this invention.

The present invention also provides a kit containing anti-DOCK180 protein antibody and/or a nucleic acid that specifically hybridizes with DNA encoding DOCK180 for each of the above-described methods. Preferably, the kit further contains an anti-CD34 antibody. A kit of this invention may comprise a secondary antibody, a labeled substance and other substances useful in performing immunological detection means, or a buffer solution, DNA polymerase and other substances useful in performing genetic engineering detection means as kit constituents.

The present invention will be described in more detail using Example, but a technical scope thereof is not limited to the Example.

EXAMPLE

<Reagents>

Recombinant human granulocyte colony stimulatory factor (rhG-CSF) was purchased from Chugai Pharmaceutical Co., Ltd. Interleukin-3 (IL-3) and stem cell factor (SCF) were purchased from PeproTech. Phycoerythrin (PE)-labeled anti-human CD14 antibody was prepared by Beckman Coulter, fluorescein-isothiocyanate (FITC)-labeled anti-human CD34 antibody by BD Biosciences. As a negative control, an antibody in a class corresponding thereto was purchased from DakoCytomation. Anti-DOCK180 antibody, goat anti-mouse IgG-HRP antibody and goat anti-rabbit IgG-HRP were purchased from Santa Cruz Biotechnology, and anti-β-actin antibody was purchased from SIGMA-ALDRICH.

Example 1

(1) Collection of Mononuclear Cells and Human CD34-Positive Cells

A bone marrow fluid-derived mononuclear cell (BM-MNC) and a peripheral blood-derived mononuclear cell (PB-MNC) were separated from a bone marrow fluid and a peripheral blood, respectively, which were collected from healthy subjects with their consent under ethical provisions, based on Ficoll-Hypaque (Amersham) gradient centrifugation. 5 μg/kg rhG-CSF was subcutaneously administered to healthy adult subjects with their consent under ethical provisions for 5 consecutive days to collect peripheral blood after mobilizing human CD34-positive cells and leukocyte fraction using blood corpuscle separating apparatus, and cryopreserve it with liquid nitrogen. A collected leukocyte fraction is denoted as apheresis product (AP). Subsequently, a mononuclear cell (AP-MNC) was separated from cryopreserved AP based on Ficoll-Hypaque (Amersham) gradient centrifugation.

Using an anti-CD34 magnetic beads antibody (Miltenyi Biotech) and magnetic cell separating system (Miltenyi Biotec), a human CD34-positive cell (BM-CD34) was purified and collected from BM-MNC. Likewise, a human CD34-positive cell (AP-CD34) was purified and collected from AP-MNC.

Furthermore, peripheral blood of healthy subjects collected with their consent under ethical provisions was mixed with 1% dextran physiological saline according to a method described in Yuo (Neutrophil, Department of Blood and Tumor, 2000, Vol. 40, pp. 10-16, Kagakuhyoronsha) and allowed to stand at room temperature for 30 minutes. Then, after fractionated granulocyte and erythrocyte in separated upper-layer suspensions were separated and collected according to Ficoll-Hypaque (Amersham) gradient centrifugation using Ficoll-Hypaque, erythrocyte was hemolyzed and removed to collect only granulocyte (GC).

(2) Flow Cytometry Analysis

BM-CD34 and AP-CD34 collected in (1), and a bone marrow blood-derived CD34-positive cell (AML-CD34) in a patient diagnosed with acute myeloid leukemia were each suspended in 0.5% cow serum albumin-added deficient RPMI 1640 medium (SIGMA-ALDRICH) with a concentration of $1 \times 10^6$ cell/mL. Afterward, 20 μg/mL PE anti-human CD14 antibody, 20 μg/mL FITC anti-human CD34 antibody and mouse IgG1 negative controls corresponding to each antibody were added to the medium and reacted on ice for 30 minutes. After the reaction, an unbound antibody was removed by centrifugal separation and resuspended in 200 μL of said medium to be analyzed using FACSCalibur (BD Biosciences) and BD Cell Quest™ Pro version5.2 (BD Biosciences). As a result, the rates of human CD34-positive cells of BM-CD34 and AP-CD34 after purification were 90% or more. The rate of CD34-positive cells in AML-CD34 was 70% or more.

(3) Measurement of DOCK180 Expression by Quantitative RT-PCR Method

Total RNAs were extracted from PB-MNC, GC, AP-MNC, AP-CD34, BM-MNC and BM-CD34 obtained in (1) (each cell numbered at $5 \times 10^6$) using RNeasy Mini Kit (QIAGEN). After treating them with RQ1 RNase free DNAse 1 (Promega), cDNAs were synthesized using SuperScript™ First-Strand Synthesis System for RT-PCR (Invitrogen). 6 μL of cDNAs obtained was mixed with a primer specific to a human DOCK180 or glyceraldehyde 3-phosphate dehydrogenase (GAPDH) (TaqMan Gene Expression Assays, Applied Biosystems) and TaqMan Universal PCR Master Mix (Applied Biosystems) so that the total volume was 25 μL. After initial denaturation (at 95° C. for 10 minutes), PCR reaction whose 1 cycle is composed of one at 95° C. for 15 seconds and one at 60° C. for 1 minute was performed 40 times. An expression level of DOCK180 mRNA in each sample was corrected by an expression level of mRNA of GAPDH, and using an expression level of 293T cells as 1000 units, the relative levels thereto were calculated.

Figure 1:
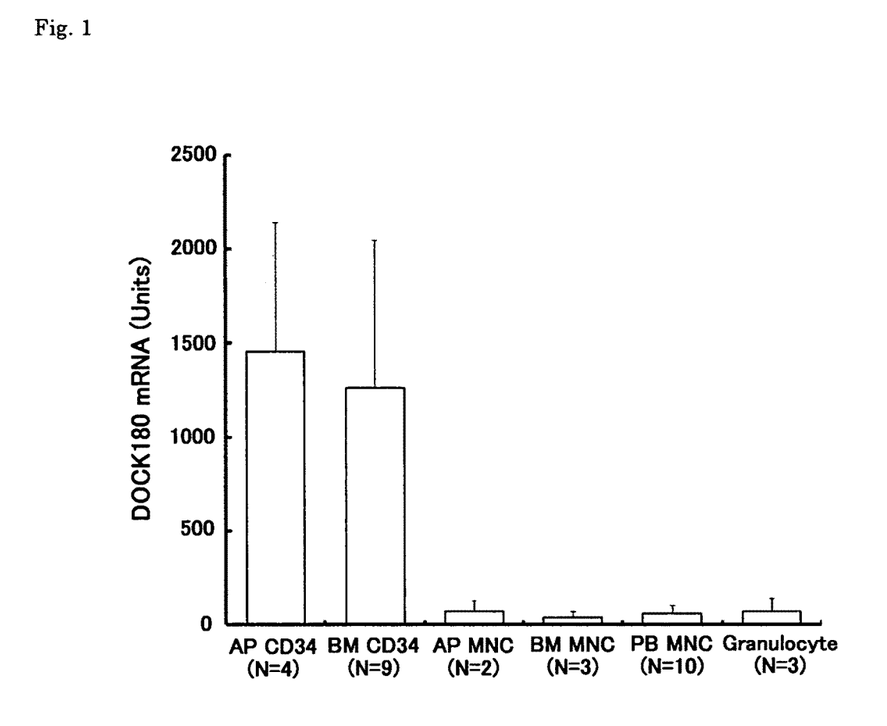
FIG. 1 is a graph showing the relative levels of DOCK180 mRNA expression in each cell by defining an expression level of DOCK180 mRNA in 293T cells measured by quantitative RT-PCR method as 1000 units. (Data as mean value and standard deviation (only forward)).

As a result, detected mRNAs of DOCK180 in PB-MNC, GC, AP-MNC and BM-MNC were extremely little, 56±47 units (mean±SD, n=10), 71±69 units (mean±SD, n=3), 69±57 units (mean±SD, n=2) and 37±35 units (mean±SD, n=3), respectively. Meanwhile, those in AP-CD34 and BM-CD34 showed highly expression at 1455±689 units (mean±SD, n=4) and 1263±783 units (mean±SD, n=9), respectively (see FIG. 1).

(4) Measurement of DOCK180 Expression by Immunoblotting

After lysing each cell type equivalent to that of AP-CD34, BM-CD34, AP-MNC and BM-MNC in (3) with lysis buffer containing 1% NP-40, supernatants were collected by centrifugal separation at 14000 rpm at 4° C. for 15 minutes to prepare protein extracts. After electrophoresis of each sample by SDS-PAGE using 7.5 to 15% polyacrylamino gradient gel (BIO-RAD), electrophoretic pattern was transferred to a nitrocellulose membrane (PALL). After blocking of the transferred membrane with 5% skim milk-added 1% Tween-phosphate buffered saline for 30 minutes, it was reacted with each primary antibody at room temperature for 2 hours. As a primary antibody, an anti-DOCK180 antibody and an anti-β-actin antibody were used. After washing the membrane, the anti-DOCK180 antibody and the anti-β-actin antibody were reacted with secondary antibodies corresponding thereto, respectively, at room temperature for 30 minutes, and each antibody was colored using ECL Western blotting detection reagent (Amersham) and imaged by LAS1000 (Fujifilm).

Figure 2:
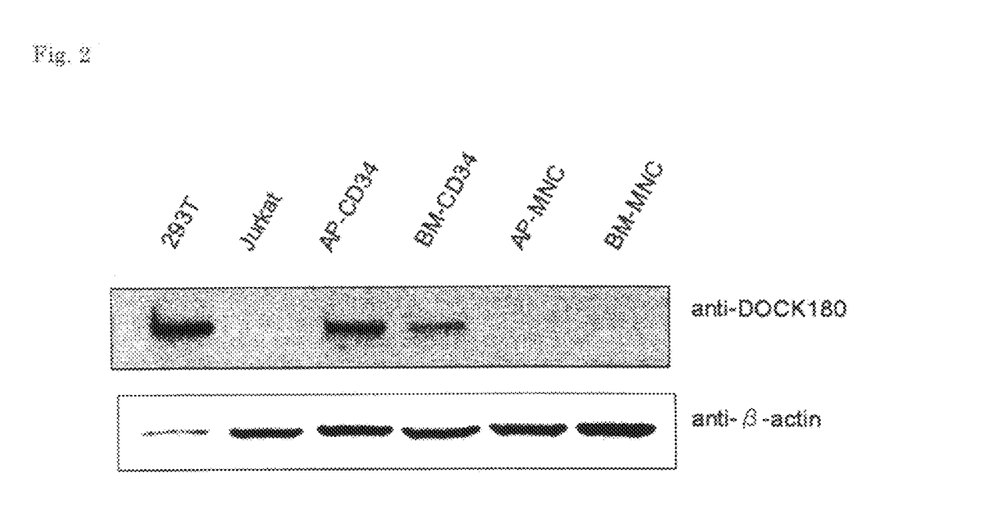
FIG. 2 is a diagram (photo) showing the results of immunoblotting to each cell prepared in Example using an anti-DOCK180 antibody. (293T cells as positive control and Jurkat cells as negative control)

As a result, as in (3), DOCK180 expression was confirmed only in AP-CD34 and BM-CD34, but no DOCK180 expression was observed in AP-MNC and BM-MNC (see FIG. 2). From these observations, a bone marrow and a peripheral blood showed DOCK180 expression only in a human CD34-positive cell.

(5) DOCK180 Expression in Acute Leukemia Cell

The total 25 cases of bone marrow fluids, composed of 3 cases of CD34-positive ALL at onset, 4 cases of recurrent CD34-positive ALL, 14 cases of CD34-positive AML at onset, 2 cases of recurrent CD34-positive AML and 2 acute blastic crisis cases of recurrent CD34-positive CML, were collected from patients with their consent under ethical provisions to extract total RNAs from the cells and examine an expression level of DOCK180 mRNA by quantitative RT-PCR method as in said (3). The results are shown in FIGS. 3 and 4.

Figure 3:
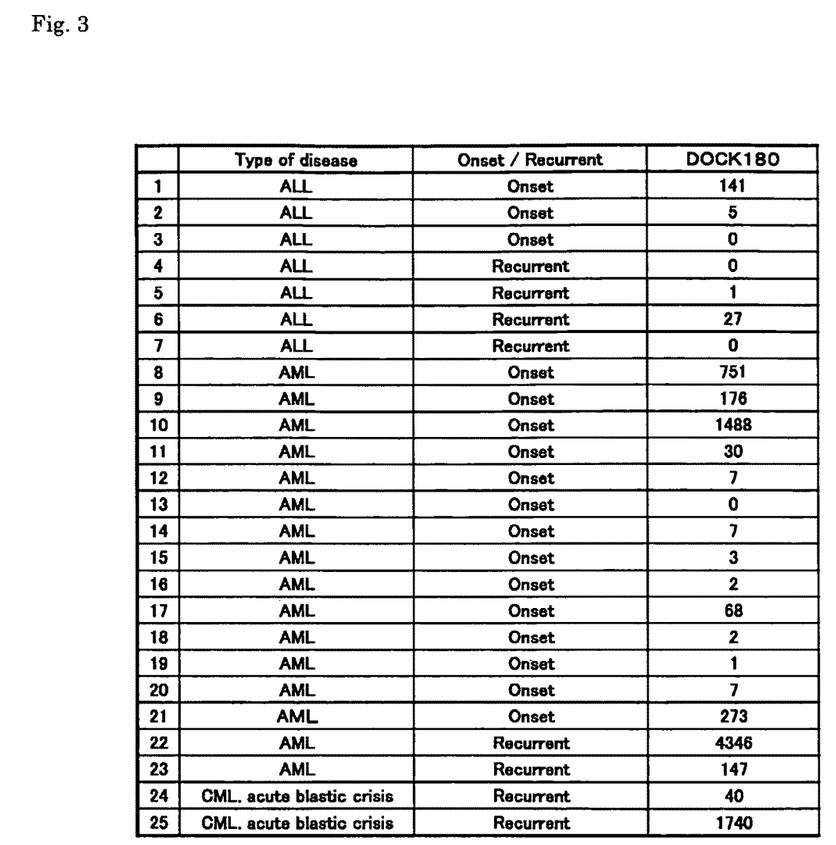
FIG. 3 is a table showing the relative levels of DOCK180 mRNA expression in 25 cases of tumor cells, composed of 3 cases of initial CD34-positive acute lymphoblastic leukemia (ALL) at onset, 4 cases of recurrent CD34-positive ALL, 14 cases of initial CD34-positive acute myeloid leukemia (AML) at onset, 2 cases of recurrent CD34-positive AML, 2 acute blastic crisis cases of recurrent CD34-positive chronic myeloid leukemia (CML) by defining an expression level of DOCK180 mRNA in 293T cells as 1000 units measured by quantitative RT-PCR method.
Figure 4:
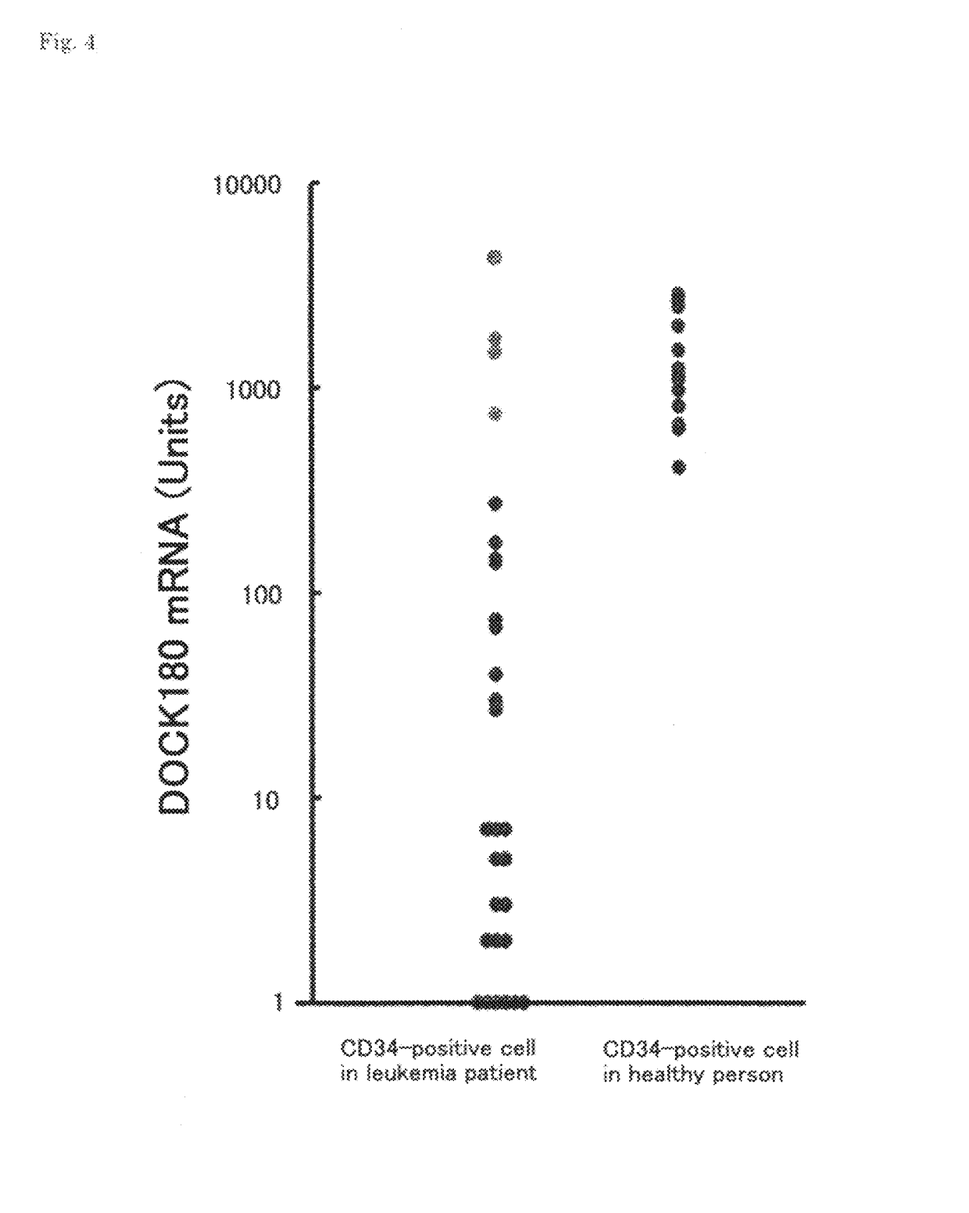
FIG. 4 is a graph showing the relative levels of DOCK180 mRNA expression in 25 cases of tumor cells, composed of 3 cases of CD34-positive ALL at onset, 4 cases of recurrent CD34-positive ALL, 14 cases of CD34-positive AML at onset, 2 cases of recurrent CD34-positive AML, 2 acute blastic crisis cases of recurrent CD34-positive CML by defining an expression level of DOCK180 mRNA in 293T cells as 1000 units measured by quantitative RT-PCR method.

In said 25 cases of bone marrow specimens in comparison with a normal BM-CD34, DOCK180 mRNA expression was low (see FIGS. 3 and 4), except for in 2 cases of CD34-positive AML at onset (No. 8 and No. 10 in FIG. 3), 1 case of recurrent CD34-positive AML (No. 22 in FIG. 3) and 1 acute blastic crisis case of recurrent CD34-positive CML (No. 25 in FIG. 3). In particular, DOCK180 mRNA expression was low in all CD34-positive ALL cases, whether at onset or recurrent. Among low-DOCK180 mRNA expression cases, 4 cases of CD34-positive AML (M0, M2, M4 or M7 case according to French-American-British classification, corresponding to No. 18, No. 23, No. 17 and No. 19 in FIG. 3) were analyzed by immunoblotting according to said (4), and no DOCK180 protein expression was found in the bone marrow specimens thereof.

(6) Changes in DOCK180 Expression Level Associated with Leukemia Remission

Figure 5:
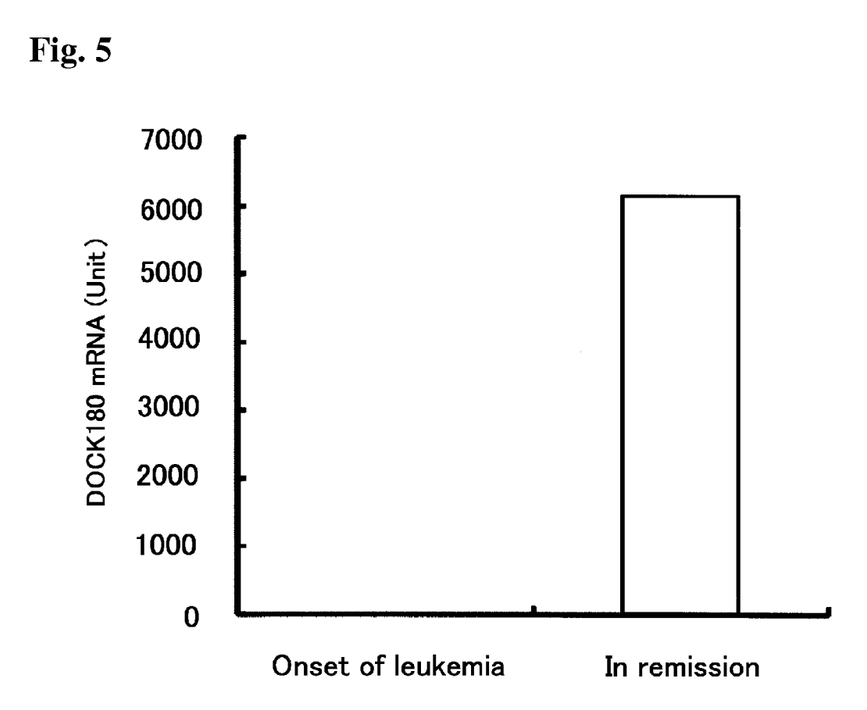
FIG. 5 is a graph showing the results of changes in expression level of DOCK180 in a CD34-positive cell of a leukemia patient in remission with treatment for leukemia measured by quantitative RT-PCR method.

Patients diagnosed with CD34-positive acute myeloid leukemia as a result of diagnosis for bone-marrow biopsy were subjected to remission-induction therapy of idamycin and cylocide for 7 days. Prior to the therapy, bone marrow in said patients contained 80% or more leukemia cells, all showing CD34-positive. DOCK180 of the bone marrow cell was measured as described above. Also, bone marrow specimens were collected from patients having certain therapeutic effects using bone-marrow biopsy having corpuscles in recovery as an index, and an expression level of DOCK180 in CD34-positive cells in remission was measured by quantitative RT-PCR as described above. As a result, patients in remission due to remission-induction therapy of idamycin and cylocide for leukemia demonstrated DOCK180 expression in CD34-positive cells (see FIG. 5).

The invention claimed is:

1. A method of detecting a leukemia cell in a blood specimen, comprising the steps of:
   a) obtaining the blood specimen from an animal,
   b) analyzing the blood specimen to detect a CD34-positive cell,
   c) isolating the CD34-positive cell from the blood specimen, and
   d) analyzing the CD34-positive cell to detect if it is DOCK180-negative, wherein a CD34-positive-DOCK180-negative cell is a leukemia cell.

2. The method of claim 1, wherein the CD34-positive-DOCK180-negative cell is detected using an anti-CD34 antibody and an anti-DOCK180 antibody.

3. The method of claim 1, wherein the leukemia cell is an acute leukemia cell.

4. The method of claim 3, wherein the acute leukemia cell is an acute lymphocytic leukemia cell.

5. A method of detecting leukemia, comprising the steps of:
   a) obtaining a blood specimen from an animal,
   b) analyzing the blood specimen to detect a CD34-positive cell,
   c) isolating the CD34-positive cell from the blood specimen, and
   d) measuring an expression level of DOCK180 in the CD34-positive cell in the blood specimen to detect leukemia.

6. The method of claim 5, wherein the expression level of DOCK180 in the CD34-positive cell in the blood specimen is compared to an expression level of DOCK180 in non-tumorigenic CD34-positive cells, and determining whether the expression level of DOCK180 protein or mRNA encoding DOCK180 in the blood specimen is 50% or less compared to that in non-tumorigenic CD34-positive cells.

7. The method of claim 5, wherein leukemia is acute leukemia.

8. The method of claim 7, wherein acute leukemia is acute lymphocytic leukemia.

9. The method of claim 1, wherein the blood specimen is selected from the group consisting of a peripheral blood sample, a bone marrow sample, a centrifugal separated blood-cell fraction sample containing CD34-positive cells, and a chemical treatment separated blood-cell fraction sample containing CD34-positive cells.

10. The method of claim 5, wherein the blood specimen is selected from the group consisting of a peripheral blood sample, a bone marrow sample, a centrifugal separated blood-cell fraction sample containing CD34-positive cells, and a chemical treatment separated blood-cell fraction sample containing CD34-positive cells.

* * * * *

UNITED STATES PATENT AND TRADEMARK OFFICE
CERTIFICATE OF CORRECTION

| | |
|---|---|
| PATENT NO. | : 8,617,804 B2 |
| APPLICATION NO. | : 12/735274 |
| DATED | : December 31, 2013 |
| INVENTOR(S) | : Takao Koike et al. |

It is certified that error appears in the above-identified patent and that said Letters Patent is hereby corrected as shown below:

On the Title Page
Item (73):
Please change the Assignee to read as follows:

-- LSIP, LLC, Tokyo JAPAN --.

Signed and Sealed this
Nineteenth Day of August, 2014

Michelle K. Lee
*Deputy Director of the United States Patent and Trademark Office*